(12) United States Patent
Salt et al.

(10) Patent No.: US 7,691,429 B2
(45) Date of Patent: Apr. 6, 2010

(54) NUTRITIONAL SUPPLEMENTS CONTAINING METHYLSELENOCYSTEINE

(75) Inventors: David Salt, Flagstaff, AZ (US); Burt D. Ensley, Newton, PA (US); Cynthia Orser, McLean, VA (US)

(73) Assignee: iBio, Inc., Newark, DE (US)

( * ) Notice: Subject to any disclaimer, the term of this patent is extended or adjusted under 35 U.S.C. 154(b) by 0 days.

(21) Appl. No.: 11/232,781

(22) Filed: Sep. 22, 2005

(65) Prior Publication Data

US 2006/0021086 A1    Jan. 26, 2006

Related U.S. Application Data

(63) Continuation of application No. 09/659,926, filed on Sep. 12, 2000, now Pat. No. 6,958,435, which is a continuation-in-part of application No. 09/041,355, filed on Mar. 12, 1998, now Pat. No. 6,117,462.

(51) Int. Cl.
*A23L 1/30* (2006.01)
*A23L 1/304* (2006.01)

(52) U.S. Cl. ............ 426/648; 424/600; 424/617; 424/702; 426/74; 426/615

(58) Field of Classification Search ............ None
See application file for complete search history.

(56) References Cited

U.S. PATENT DOCUMENTS 6,117,462 A * 9/2000 Ensley et al. ............ 426/74
6,270,809 B1 * 8/2001 Ensley et al. ............ 424/617

OTHER PUBLICATIONS

Salt et al (Biotechnology, vol. 13, pp. 468-474, (1995).*
Banuelos et al. Journal of Environmental Quality (1990), 19:4, pp. 772-777.*
Xiao et al. J. Agri. Food Chemistry (1995) 43:1754-1757.*

* cited by examiner

*Primary Examiner*—Medina A Ibrahim
(74) *Attorney, Agent, or Firm*—Fish & Richardson P.C.

(57) ABSTRACT

A method of producing metal-rich plants for the production of nutritional supplements. Edible plants are placed in a growth environment containing metal, and are cultivated in a fashion which enhances the uptake of metal into edible portions of the plants. The plants are then harvested, and may be eaten directly or processed into capsule or tablet form, in order to obtain the metallic nutrients so incorporated.

6 Claims, 6 Drawing Sheets

NUTRITIONAL SUPPLEMENTS CONTAINING METHYLSELENOCYSTEINE

The present application is a Continuation of U.S. Ser. No. 09/659,926, filed Sep. 12, 2000, now U.S. Pat. No. 6,958,435, which is a Continuation-in-part of patent application U.S. Ser. No. 09/041,355, filed Mar. 12, 1998, now issued as U.S. Pat. No. 6,117,462, the entire contents of which are incorporated herein by reference.

BACKGROUND OF THE INVENTION

The human body requires at least small amounts of a number of metals in order to maintain health. The diets of many people do not provide sufficient quantities of these metals, and such people benefit from the addition of nutritional supplements to their diets. However, it can be difficult to produce supplements that provide metals in a metabolically available form.

Even for metals that are relatively easy to provide in a metabolically available form, some consumers have an aversion to ingesting chemicals or foods that are perceived as having been artificially processed. Such consumers tend to prefer to eat plant foods, which are naturally high in the requisite metals. However, metal-rich edible plants can be difficult to obtain, and metal concentrations tend to be low, so that a large quantity must be eaten in order to obtain sufficient quantities of the metals. These drawbacks become prohibitive when the large number of metals which are beneficial to human health is considered.

An ideal dietary supplement would be an edible plant that contains high concentrations of several beneficial metals, in concentration ratios similar to the ratios considered most beneficial to humans, and contained negligble quantities of toxins. This plant would ideally be easily harvestable in a form that could be eaten fresh or dried, or alternatively would be used to form metal-rich tablets or capsules which could be taken as nutritional supplements. Unfortunately, no such naturally-occurring plant is known.

Selenium is an essential trace mineral for humans and animals and provides benefits including reduced cancer risk, reduced cardiovascular disease risk, improved immune system function, and increased resistance to viral infections. Some attempts have been made to increase the level of selenium present in garlic (Ip et al., *Cancer Research (Suppl.)* 54:1957, April, 1994) and in brussels sprouts (Stoewsand, et al., *Cancer Letters* 45:43, 1989), but achievable concentrations were found to be quite small. These two studies, which tested the effects of selenium on mammary carcinogenesis in rats, used dietary fractions of 2% for garlic and 20% for selenium on mammary carcinogenesis in rats, used dietary fractions of 2% for garlic and 20% for brussels sprouts in order to achieve sufficient selenium levels. These would represent prohibitively large quantities of a single food in a normal human diet.

SUMMARY OF THE INVENTION

The present invention pertains to a method of producing plant foods and nutritional supplements that are rich in metals. In one aspect, the invention comprises manipulating the environment and growth of an edible crop plant to cause it to accumulate nutritionally significant amounts of metal in its edible portions, and then harvesting the metal-rich edible portions. These metal-rich portions may be themselves used as food or may be subject to further processing for incorporation into nutritional supplements. The growth environment may already contain appropriate amounts of desired metals, or such may be added before or during the cultivation process. Exemplary metals contemplated for use with the invention, include iron, zinc, manganese, chromium, selenium, vanadium, molybdenum, boron, titanium, and germanium. The first five of these are considered particularly advantageous, but any nutritionally valuable metal which can be caused to accumulate in the edible portions of a plant is suitable for the practice of the invention.

It may be desirable to manipulate the growing environment of the plant during cultivation to enhance uptake of metals. For example, plants can accumulate high levels of selenium, but these levels are dependent on the level of selenium in the soil. Soil selenium content varies geographically from extremely high levels (>100 mg/kg) to very low levels (0.01 mg/kg). The variable levels of selenium in natural sources created a need for nutritional supplementation of selenium, most of them inorganic forms of selenium. Plants are desirable because they can convert inorganic selenium to organic forms, for example seleno amino acids, the most beneficial nutritional form for humans.

Some methods of enhancing metal uptake in plants are described in U.S. Pat. Nos. 5,785,735; 5,917,117; and 6,117,462, each of which is incorporated herein by reference. Included in some embodiments of the present invention is a step of exposing the plant to an inducing agent which induces hyperaccumulation of metals. In preferred embodiments, the inducing agent is an organic acid, such as citric acid, acetic acid, malic acid, salicylic acid, or succinic acid.

Many plants are suitable for use with the present invention. Crop plants that produce a significant biomass are preferred, since such plants are frequently able to incorporate larger quantities of metals in their edible portions, but any plant that can accumulate sufficiently high levels of metals in edible portions may be used in the practice of the invention. In particular, some preferred embodiments use crop plants of the family Brassicaceae. Within this family, plants of genera *Brassica, Thlaspi, Alyssum*, and *Eruca* are preferred. Further preferred are species *Brassica juncea, Brassica nigra, Brassica campestris, Brassica carinata, Brassica napus*, and *Brassica oleracea*.

In a related aspect, the invention comprises an isolated, edible plant which has been exposed to an inducing agent, and thereby induced to accumulate more metal in its edible portions than it would in the absence of the inducing agent. Preferred inducing agents include organic acids, such as citric acid, malic acid, acetic acid, salicylic acid, or succinic acid. Metal may be added to the growing environment of the plant. For example, one or more of iron, zinc, manganese, chromium, selenium, vanadium, molybdenum, boron, titanium, and germanium may be added.

In another aspect, the invention comprises a nutritional supplement comprising edible portions of a plant that has been induced to hyperaccumulate metals. This induction may have been accomplished by exposing the plant to an inducing agent, such as the organic acids citric acid, malic acid, acetic acid, salicylic acid, or succinic acid. Ideally, the plant will accumulate one or more nutritionally valuable metals in amounts of at least 400 ppm metal (dry weight). In one embodiment, the plant is a member of the family Brassicaceae, such as species *Brassica juncea, Brassica oleracea*, and *Brassica carinata*.

In yet another aspect, the invention comprises an isolated, edible plant which contains high levels of nutritionally valuable metals: at least 400 ppm total metal (dry weight). In a preferred embodiment, the plant is a member of the family Brassicaceae, such as species *Brassica juncea, Brassica*

*oleracea*, and *Brassica carinata*. In some preferred embodiments, the plant into which the metal is accumulated is a transgenic plant that has been genetically engineered to express a gene encoding a protein that promotes formation of a non-toxic metal metabolite. For example, certain preferred transgenic plants express selenocysteine methyltransferase, and therefore accumulate higher levels of methylselenocysteine than they would if they were not so engineered.

In still another aspect, the invention comprises a method for producing nutritional supplements. The method comprises the steps of identifying a growth environment containing one or more metals, placing an edible crop plant in contact with that environment, cultivating the plant in a way that allows it to accumulate metal from the environment, harvesting the edible portions of the plant, and incorporating the harvested portions into a nutritional supplement. The growth environment may contain these metals before introduction of the plant, or they may be added before or during the cultivation process. Exemplary metals are iron, zinc, manganese, chromium, selenium, vanadium, molybdenum, boron, titanium, and germanium, with the first five of these being preferred. The cultivation process may include exposing the plant to an inducing agent in order to induce it to accumulate metals; for example, the inducing agent may be an organic acid such as citric acid, acetic acid, malic acid, salicylic acid, or succinic acid. The plant is preferably a member of the family Brassicaceae, such as species *Brassica juncea*, *Brassica oleracea*, and *Brassica carinata*.

Definitions

An "isolated plant," as that term is used herein, refers to a plant which has been cultivated by human agency, as distinct from one which has germinated and grown in the wild without human intervention. After a plant has been removed from its growth environment, it is described as having been "harvested."

"Nutritionally valuable" metals, as that term is used herein, are metals that are believed to be desirable for human consumption in some quantity. The fact that a metal is toxic at some dosage level does not preclude that metal from being healthful and/or desirable at a different dosage level, and therefore, such metals may still be considered nutritionally valuable. It is also recognized that considerable variation may exist in the amount of a metal which is healthful to different individuals; for example, the USDA recommended dietary allowances (RDA) of iron, zinc and selenium are substantially higher for women who are pregnant or lactating. A "nutritionally significant" quantity of a metal is an amount large enough to affect the health of at least some individuals, or at least 10% of the USDA RDA or other recommended therapeutic dose for the metal.

The term "metal," as it is used herein, includes elemental metals, metal ions, and compounds containing metal atoms.

Unless otherwise indicated, concentrations of metals in plants are dry weight concentrations. The unit of concentration "ppm" indicates parts per million.

The term "soil," as it is used herein, refers to any environment that can serve as a growth environment for plants. In particular, this term includes both conventional soil and hydroponic growth environments.

BRIEF DESCRIPTION OF THE DRAWING

The invention is described with reference to the several figures of the drawing, in which

FIG. 6 shows the solubility of selenium from plants, yeast, and a mineral supplement.

DETAILED DESCRIPTION OF CERTAIN PREFERRED EMBODIMENTS

Figure 1:
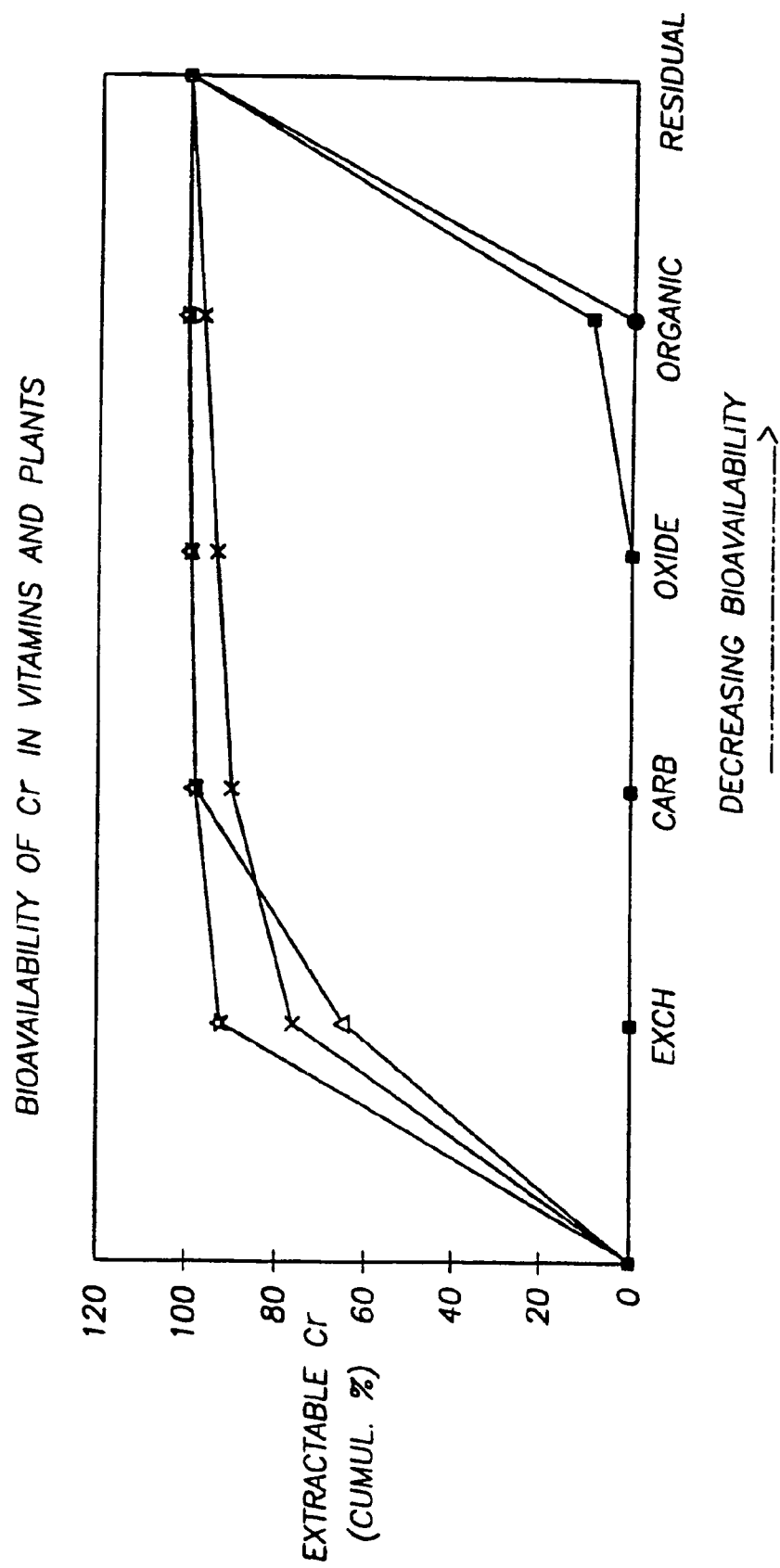
FIG. 1 depicts the bioavailability of chromium in plants according to the invention and in commercially available nutritional supplements.

Those of ordinary skill in the art will appreciate that a variety of methods are available for accumulating metals into plants. Certain edible plants will naturally accumulate metals in their edible portions when grown in environments containing sufficient levels of the metals. However, such environments can be uncommon, and in particular, it is difficult or impossible to find a naturally-occurring environment that will cause plants to take up several metals in healthful proportions for human consumption, even when uptake is stimulated by human intervention. Furthermore, there is variability in the amount of metal accrued by different plants within a population of naturally-growing plants, the extent of accumulation typically is not reproducible, and the amount of accumulation cannot be controlled by human observers.

The present invention provides strategies that remedy these problems that adhere uniform and reproducible accumulation of controllable amounts of metal in edible plants. Particularly preferred approaches to stimulating metal uptake are described, for example, in U.S. application patent Nos. 5,809,693 (which describes methods of promoting metal uptake by contacting plants with certain microorganisms), 5,785,735 (which describes various methods of manipulating the soil environment) and 5,917,117 (which describes certain inducing agents useful for stimulating high levels of metal accumulation).

The aims of the present invention may require certain modifications or limitations of the above-described known methods for stimulating metal uptake. For example, since the present invention describes nutritional supplements that are to be eaten by human beings, it is important that the plants not contain levels of the metals, or of any other substances, that are toxic to humans. For this reason, nontoxic organic acids are preferred inducing agents in the current invention. The Examples below disclose experimental results of metal uptake using citric acid as an inducing agent, but the use of other nontoxic organic acids, for example, acetic acid, succinic acid, salicylic acid, or malic acid, is also contemplated within the scope of the invention.

The invention can be used to provide dietary supplements which supply any nutritionally valuable metal which can be induced to enter the edible portions of a plant in nutritionally significant quantities. The U.S. Recommended Dietary Allowances (RDA) for selected minerals, as determined by the U.S. Department of Agriculture for males age 25-50, as well as some literature recommended values for minerals not having RDAs are given in Table 1. While dietary supplements need not contain exactly these quantities of metals, these data provide guidelines on what constitute nutritionally significant quantities of various metals.

TABLE 1

| Mineral | USRDA or therapeutic dose† (mg) |
|---|---|
| Fe | 10 |
| Zn | 15 |
| Mn | 2† |
| Cr | 0.20† |
| Se | 0.07-0.20† |

As mentioned above, the present invention encompasses the recognition that certain edible plants can accumulate metals in their edible portions. Without wishing to be bound by any particular theory, the present inventors propose that the accumulation process involves "demineralization" of the metals, so that their bioavailability is increased. For example, chromium is believed to move from roots to shoots of plants by binding to phytochelatins and organic acids. At least one organic acid, picolinic acid, has been shown to increase the bioavailability of chromium in humans. Selenium, present in soil, can be converted to nontoxic seleno-amino acids such as selenocystein and selenomethionine. Selenocysteine is not incorporated into proteins. A co-translational process yields a t-RNA-bound selenocysteine. Selenomethionine on the other hand, is incorporated non specifically into methionine-containing proteins during protein synthesis. Selenomethionine can also generate organically complex and active selenocysteine. These seleno-amino acids are more stable in the body than inorganic forms of selenium.

Further, some metals may provide increased benefits through a synergistic effect with other plant components. For example, it is believed that dietary selenium helps to protect against cancer. Recent studies have suggested that this effect may be intensified when selenium is taken with various antioxidants (see, for example, Salonen et al., *British Medical Journal* 290:417, 1985). Selenocysteine is located in the active centers of several antioxidant enzymes. Many relevant antioxidants are already present in certain plants useful for the invention (e.g., Brassicaceae, in Fahey, et al., *Proc. Natl. Acad. Sci. USA* 94:10367, 1997). Without making any claims of pharmaceutical efficacy, we note that one advantage of certain nutritional supplements of the present invention is that they are expected to have protective antioxidant effects. Similarly, iron uptake in humans can be enhanced by the presence of vitamin C (Davidsson, et al., *Ped. Res.* 36(6):816, 1994), and it may therefore be beneficial to use plants naturally rich in this vitamin for accumulating iron for the purpose of making dietary supplements. Similar synergistic effects may exist for other metals and other plant components.

In broad terms, the methods of the invention comprise the following steps: A growth environment containing desired metallic species is identified and/or created. An edible plant capable of accumulating the desired metals is then provided, and cultivated in the growth environment. While simply providing the enriched growth environment may be sufficient to yield accumulation of sufficient quantities of metal, it is often desirable to use an inducing agent to enhance the uptake of metal by the plant. While the exact mechanism by which such an agent enhances metal uptake need not be understood in order to practice the invention, it is often found that good inducing agents are mild to severe stressors of the plant. For example, plants may be induced to hyperaccumulate metal by very high metal concentrations in the soil, or by the addition of acids and/or chelators to the soil. In the Examples that follow, citric acid is used as an inducing agent.

The growth environment of the plant may be manipulated at various points during growth in order to control the amount of metal which is accumulated by the plant. For example, it may be desirable that the plant grow to a certain size before the addition of an inducing agent which causes hyperaccumulation of metals in the environment. In particular, it is often desirable to grow the plants for 4.5-6 weeks before the addition of the inducing agent. The inducing agent can comprise the addition of a salt of the metal, for example sodium selenate or potassium selenate, and an organic acid, for example citrate. The addition of inducing agents changes the growth environment of the plant enough to stimulate the plant into accumulating metals.

The most preferred embodiments of the invention employ hydroponic growth environments because these environments are particularly easy to control. Desired metals and other additives can be added to such environments in precise amounts, at carefully controlled times, without also adding undesirable contaminants. Plants cultivated in outdoor fields may be subject to variation due to previous soil treatments, acid rain, or other factors. Nevertheless, the invention may be practiced using any soil environment which contains the desired metals in suitable quantities.

Many different plants can be used in the practice of the invention. It has been found that plants of the family Brassicaceae, particularly those of genera *Brassica*, *Thlaspi*, *Alyssum*, and *Eruca*, are capable of accumulating metal in their shoots and/or leaves. Particularly preferred are the species *Brassica juncea*, *Brassica nigra*, *Brassica campestris*, *Brassica carinata*, *Brassica napus*, and *Brassica oleracea*. The metal-accumulating properties of these plants may be further enhanced by the use of genetic manipulation. Such techniques are further described in U.S. patent application No. 5,785,735 and include EMS mutagenesis and gene transfer from a variety of plant and animal species.

In one particularly preferred embodiment of the present invention, genetically engineered plants are employed for the accumulation of selenium. In particular, a described in Example 5, a transgenic *B. juncea* plant can be produced that has gained the capacity to accumulate Se-methyl selenocysteine when exposed to selenite. Without wishing to be bound by any particular theory, we propose that selenium accumulation in plants is controlled by both Se uptake from the growth environment and formation of non-toxic Se metabolites, particularly in Se-methylselenocysteine, the plant tissues. According to the present invention, Se uptake into plant tissues is enhanced by expression of a gene (e.g., the selenocysteine methyl transferase gene) that increases the production of such non-toxic Se metabolites with in the plant. The invention therefore provides genetically engineered plants that have been manipulated to express a gene that is not naturally found within those plants and that increases production of non-toxic Se metabolites. In particularly preferred embodiments, the plants are *B. juncea*, the gene is selenocysteine methyl transferase, and/or the engineered plants accumulate at least about 2 fold more selenium on average as compared with comparable non-engineered plants. Preferably, the engineered plants accumulate at least about 400 ppm selenium.

When cultivating *Brassica juncea* plants in a hydroponic or potting mix environment, one method of delivering metal and optional inducing agents is via an irrigation system. In one such system, the plants can be supplied with fertilizer, metal-containing solutions, and small amounts of an inducing agent such as citric acid for approximately four weeks, until the plants have attained a desirable size. At that time, an application of larger amounts of metal-containing solutions and the inducing agent can be used to cause the plants to hyperaccumulate large quantities of metal. The irrigation technique can also be used in conventional soil, which is seeded using available agricultural practices. It is desirable to select a sandy soil with low exchangeable aluminum, in order to minimize accumulation of this possibly harmful element in the edible portions of the plant.

Once the plant has accumulated one or more nutritionally valuable metals in its edible portions, these portions can be harvested using standard agricultural practices for food crops. These portions can then be eaten directly in order to obtain the nutritive metals, or they may be dried and incorporated into other forms such as capsules, tablets, powders, gels, or liquids, using techniques well-known to those skilled in the art. The edible plant portions may be formulated with other foods or liquids to provide premeasured supplemental foods, e.g., single-serving bars. Flavorings, binders, protein, complex carbohydrates, and the like may be added as needed. Further, pharmaceutical elements such as antibiotics may be incorporated into the supplements if desired.

In a preferred embodiment, the quantities of nutritionally valuable metals that have been accumulated in the plants are measured, and the plants are dried and mixed with dried plant material which has not been manipulated to accumulate metal. The resulting mixture can then be incorporated into capsules, tablets, or similar formulations by any method known in the art. By tailoring the ratio of enriched to unenriched plants in view of the level of accumulation of the enriched plants, the dosage of the mixture can be precisely controlled, an advantage of this method of formulating nutritional supplements. There have been reported cases of nutritional supplements containing much greater quantities of some metals than reported on the label (see, for example, JAMA 275:1087, 1996). "Natural" supplements are particularly vulnerable to this type of variability, since the plants from which they are generally made are subject to significant variability. The mixing method described above allows this safety hazard to be minimized or eliminated.

EXAMPLES

Example 1—Hydroponic Growth

The hydroponic system was created by germinating *B. juncea* seeds in rock wool blocks. The rock wool blocks were hydrated by placing them in a 10×23×2 inch tray containing water. Nutrients were added to the rock wool every five days by adding 100 ml of nutrient solution (2 g Hydrosol☐ and 2.5 g CaNO$_3$, dissolved in 1 L of water) to each rock wool block (2 plants/block). After 3.5 weeks growth, 3 L of solution containing citric acid and one desired micronutrient was added to the tray containing the rock wool blocks. Fe, Mn and Zn were each added using the sulfate salts (FeSO$_4$ MnSO$_4$, and ZnSO$_4$) at concentrations of 0.5, 2.0, or 10 g/L of the metal. Cr and Se were each added as CrCl$_3$ and Na$_2$SeO$_4$ salts, respectively, each at 0.1 and 1.0 g Cr or Se/L. The citric acid was added at a concentration equimolar to the respective micronutrient. One week after the treatments were added the plants were harvested by cutting the stems 1 cm above the rock wool. The plant samples were placed in paper bags, dried at 60° C. and ground to 20 mesh. The dried and ground plant samples were wet ashed using a nitric/perchloric acid digestion and analyzed for metal content using inductively-coupled plasma optical emission spectroscopy (ICP). Results of this analysis are shown in Table 2. It will be seen that the addition of citric acid usually increased the level of metal uptake considerably, particularly when smaller amounts of metal were added to the growth environment. The plants grown according to this technique have high nutrient levels compared to conventionally grown plants. Their edible portions could be incorporated by techniques well-known in the art into capsule or tablet form, or could be eaten fresh or dried, in order to obtain metallic nutrients.

TABLE 2

| Metal Concentration | Citric Acid (equimolar to metal) | Fe | ±std err. | Mn | ±std err. | Zn | ±std err. | Cr | ±std err. | Se | ±std err. |
|---|---|---|---|---|---|---|---|---|---|---|---|
| | | | | | | (All values in mg/kg) | | | | | |
| 10 g/L | no | 27707 | 11419 | 8531 | 1437 | 41167 | 6553 | | | | |
| 10 g/L | yes | 15545 | 877 | 15782 | 2865 | 34657 | 1798 | | | | |
| 2 g/L | no | 950 | 225 | 3557 | 25 | 3854 | 1281 | | | | |
| 2 g/L | yes | 4293 | 240 | 7881 | 2711 | 20493 | 2844 | | | | |
| 0.5 g/L | no | 132 | 20 | 4090 | 1292 | 2529 | 1529 | | | | |
| 0.5 g/L | 0yes | 252 | 145 | 950 | 253 | 2626 | 838 | | | | |
| 1.0 g/L | no | | | | | | | 715 | 559 | | |
| 1.0 g/L | yes | | | | | | | 4700 | 856 | | |
| 0.1 g/L | no | | | | | | | 0 | | 754 | 124 |
| 0.1 g/L | yes | | | | | | | 0 | | 537 | 537 |

Example 2—Field Growth

*B. juncea* plants were broadcast seeded in the field at the rate of 12 lbs. seed/acre. The plots were fertilized with 300, 150 and 150 lbs/acre N, P, and K, respectively. In addition the plots received weekly fertilization additions of Blu-Gro™ at the rate of 1 ml/ft$^2$ applied through the overhead sprinkler irrigation system. After 4 weeks growth (at the onset of flowering), citric acid was applied to the plot through the sprinkler system at the rate of 2.5 mmol citric acid/kg soil (500 mmol/m$^2$). One week after treatment the plants were harvested by cutting the stem at the soil surface. The plant tissue was dried at 60° C., ground and analyzed as previously described. Results of this analysis are shown in Table 3. It will be seen that the dried plants contained high levels of the nutrients potassium and calcium as a result of the manipulation of their growth environment. The edible portions of the plants can be incorporated by techniques well-known in the art into capsule or tablet form, or can be eaten fresh or dried, in order to obtain these nutrients.

TABLE 3

| | Metal: | | | | | | | |
|---|---|---|---|---|---|---|---|---|
| | Ca | Cu | Fe | K | Mg | Mn | S | Zn |
| Shoot concentration (mg/kg) | 20,467 | 19 | 584 | 42,437 | 3,691 | 225 | 8,034 | 778 |

Example 3—Potting Mix

B. juncea seeds were planted in 3.5" diameter pots containing Pro-Mix (commercial potting mix). The plants were thinned to 2 plants/pot 3 days after seedling emergence. After 4 weeks growth three pots were placed into a 10"☐23"☐2" plastic tray with 3 L of water containing Cr, Fe, or Zn at 5 g/L. Citric acid was added to the trays in equimolar concentrations to the applied metal. The plants were harvested one week after the metal and citric acid additions. The plant tissue was dried, ground, and analyzed as previously described. Results of this analysis are shown in Table 4. It will be seen that the plants contained large quantities of the added nutrients as a result of the soil treatment. Their edible portions can be incorporated by techniques well-known in the art into capsule or tablet form, or can be eaten fresh or dried, in order to obtain these nutrients.

TABLE 4

| Treatment | Cr (mg/kg) | Fe (mg/kg) | Zn (mg/kg) |
|---|---|---|---|
| Cr (5 g/L) | 50,900 | 357 | 300 |
| Fe (5 g/L) | ND | 29,900 | 187 |
| Zn (5 g/L) | ND | 663 | 53,800 |
| Fe (5 g/L) + Zn (5 g/L) + Cr (5 g/L) | 9610 | 8560 | 11,800 |

Example 4—Increased Bioavailability of Metals

B. juncea plants were grown in 3.5" diameter pots containing Pro-Mix (commercial potting mix). The plants were thinned to 2 plants per pot 3 days after emergence. After four weeks growth, metals were applied in two modes. For those plants having metals applied to the pan, three pots were placed into a 10"×23"×2" plastic tray with 3 L of water containing Cr, Fe, or Zn at 5 g/L. For those plants having metals applied to the pot, 20 mL of 0.5 M solution of each of metal was applied to the soil surface in each pot. Citric acid was added to the trays or pots in equimolar concentrations to the applied metal. The plants were harvested one week after the metal and citric acid additions. The plant tissue was dried and ground. Duplicate samples of each metal/plant combination were then extracted sequentially using the procedure of Tessier, et al. (*Analyt. Chem.* 51(7):844, 1979, incorporated herein by reference) to assess the degree of bioavailability as described by Berti et al. (*Proc. 3rd Int'l Conf. Biogeochem. of Trace Elements*, Paris, May 1995, incorporated herein by reference). The sequential extraction procedure uses five extractants that are operationally defined to selectively extract a certain fraction of the metal, removing the more bioavailable forms first and less bioavailable forms with each subsequent extraction. The fractions extracted and the extractant used are the following: (1) exchangeable—metals that are readily extracted with 1M $MgCl_2$ (2) carbonate—metals that are readily extracted with 1N NaOAc at pH 5, (3) oxide—metals that are readily extracted with 0.04M hydroxylamine hydrochloride at pH 0, (4) organic—metals that are readily extracted with 30% hydrogen peroxide and 0.1N $HNO_3$, (5) residual—metals that are readily extracted with concentrated nitric acid.

For comparison, duplicate samples of four over-the-counter mineral supplements (Centrum multivitamin, Zn picolinate, GNC G.T.F. Chromium, and Cr picolinate) were similarly extracted to assess their degree of bioavailability. Results are shown in FIGS. 1-3.

FIG. 1 presents bioavailability data for chromium. Data for commercially available vitamin supplements are represented by circles for Centrum multivitamins, squares for GNC G.T.F. Chromium, and triangles for Cr picolinate. X's represent data for plants that had chromium applied to the pan holding the pots, and stars represent data for plants that had iron, zinc, and chromium applied directly to the pot.

Figure 2:
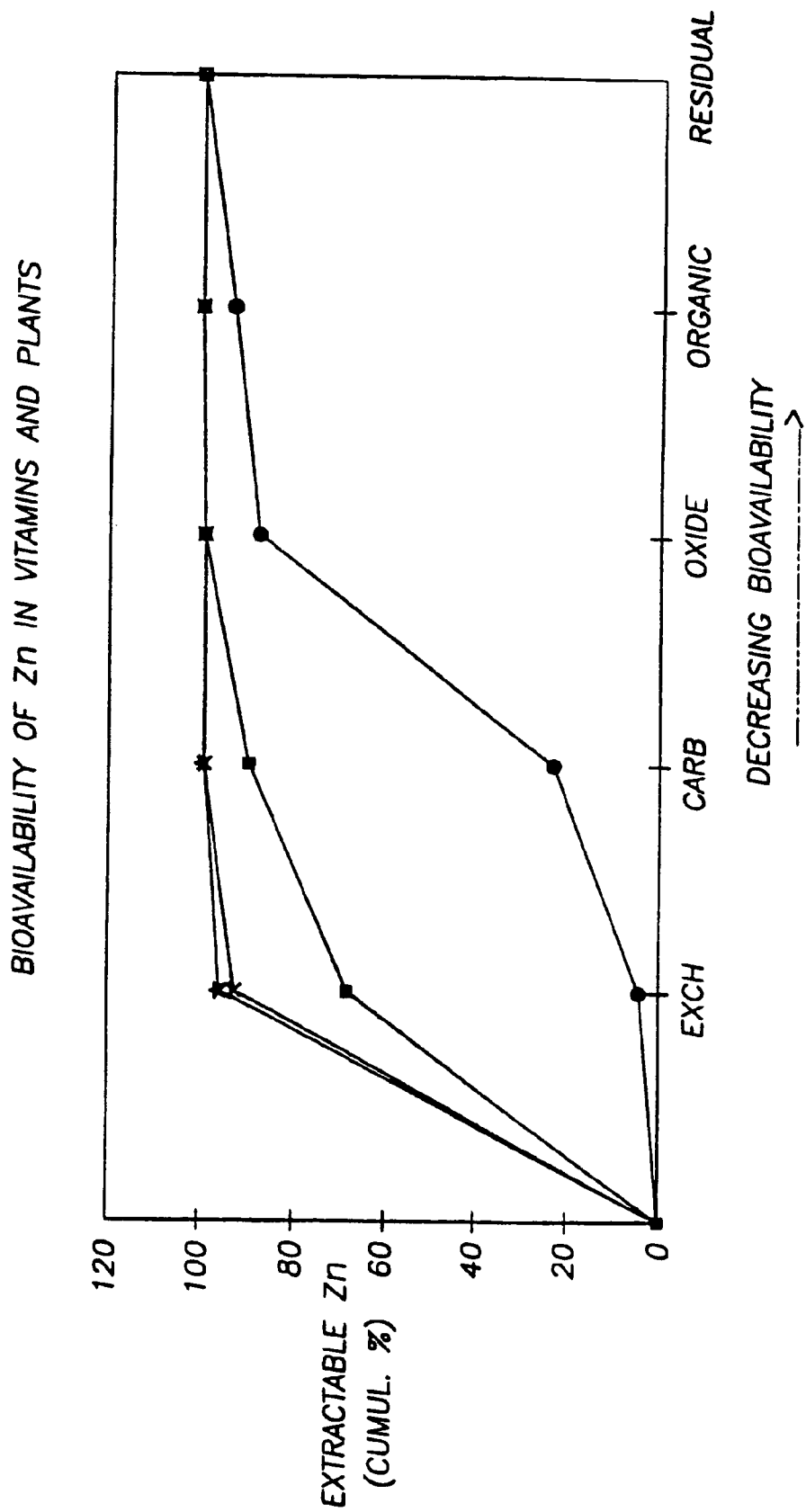
FIG. 2 depicts the bioavailability of zinc in plants according to the invention and in commercially available nutritional supplements.

FIG. 2 presents bioavailability data for zinc. Data for commercially available vitamin supplements are represented by circles for Centrum multivitamins, and squares for Zn picolinate. Triangles represent data for plants that had zinc applied to the pan holding the pots, x's represent data for plants that had zinc applied directly to the pot, and stars represent data for plants that had iron, zinc, and chromium applied directly to the pot.

Figure 3:
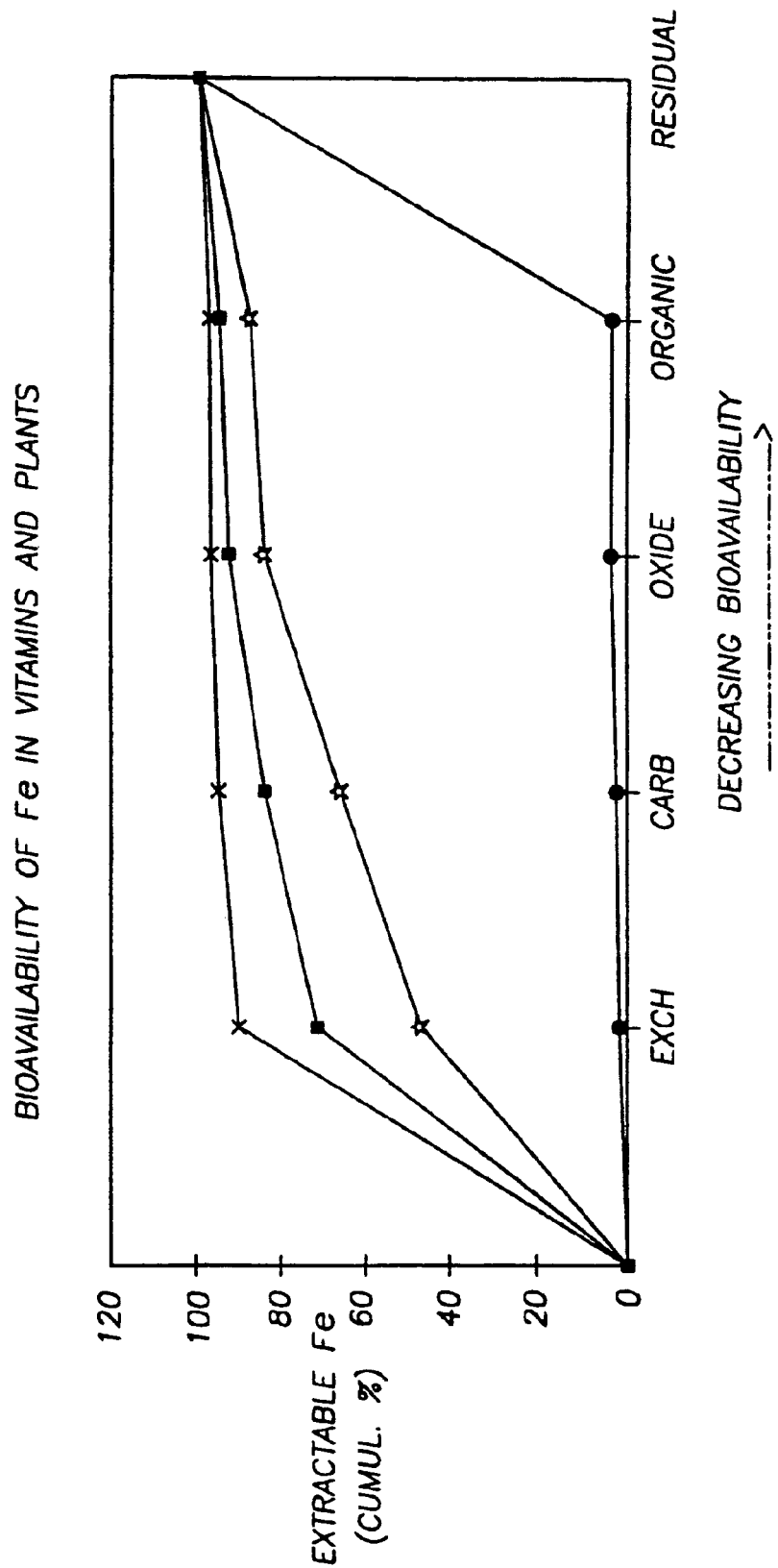
FIG. 3 depicts the bioavailability of iron in plants according to the invention and in commercially available nutritional supplements.

FIG. 3 presents bioavailability data for iron. Data are represented by circles for commercially available Centrum multivitamins. Squares represent data for plants that had iron applied to the pan holding the pots, x's represent data for plants that had iron applied directly to the pot, and stars represent data for plants that had iron, zinc, and chromium applied directly to the pot.

It will be seen that each of the three metals accumulated in the plant supplements is more bioavailable than several leading mineral supplements.

Example 5—Genetic Engineering of Plants to Increase Se Accumulation

The major Se-containing compound in accumulator species of *Astragalus* (*A. bisulcatus*) is Se-methselenocysteine [$CH_3$—Se—$CH_2$—$CHNH_2$—COOH], levels of which have been found to be significantly higher in accumulator compared to non accumulator species (Trelease et al., *Science* 132:618, 1960; Virupaksha et al., *Biochim. Biophy. Acta* 107: 69, 1965; Shrift et al., *Biochim. Biophy Acta.* 100:65, 1965).

This finding suggests that accumulator and non accumulator plants differ in their capacity to synthesize this nontoxic dead end Se metabolite. Biochemical studies on accumulator species of *Astragalus* have shown that Se-methylselenocysteine is formed by the methylation of selenocystein (Chen et al., 1970; Chow et al., ab 1972: Neuthierl and Bock, 1996). It has been proposed that it is the ability of accumulator *Astragalus* accumulator species funnel Se into methylselenocysteine, a nontoxic dead end Se metabolite. This is achieved by increased expression of the enzyme selenocysteine methyltransferase. To reduce the flow of Se away from selenocysteine towards methionine accumulator *Astragalus* also contains a modified cystathionine-y-synthase enzyme able to select against selenocysteine as a substrate.

A two-fold strategy will be used to clone selenocysteine methyltransferase from *A. bisulcatus*. We will functionally complement an *E. coli* mutant (MetE available from the Salmonella Genetics Stock Center, strain SH259) lacking methionine synthase with the *A. bisulcatus* cDNA library. We will also screen for *A. bisulcatus* cDNA's capable of imparting resistance to selenocystine.

Cloning of plant genes by function complementation in *E. coli* has proved to be a very powerful technique (Murillo et al., 1995; Murillo et al., *Arch Biochem. Biophys.* 323:195, 1995; Setya et al., *Proc. Natl. Acad. Sci. USA* 93:13383, 1996; Leustek et al., *J. Biol. Chem.* 272:2744), hyperaccumulator *T. goesingense* (Yan et al., abc 1997).

In plants and bacteria, methionine ($CH_3$—S—$CH_2$—$CHNH_2$—COOH) is synthesized from homocysteine (SH—$CH_2$—$CH_2$—$CHNH_2$—COOH) by the transfer of a methyl group from S-methyltetrahydropteroyltrigluamate catalyzed by the enzyme methionine synthase (Eichel et al., 1995). Because of the similarity in structure between homocysteine and selenocysteine, we propose that selenocystein methyl transferase should be able to functionally complement the lack of methionine synthase in the mutant *E. coli* Met E. Therefore, the A-Yes cDNA library from *A. bisulcatus* will be used to screen for clones that suppress the methionine requirement of *E. coli* strain MetE.

Figure 4:
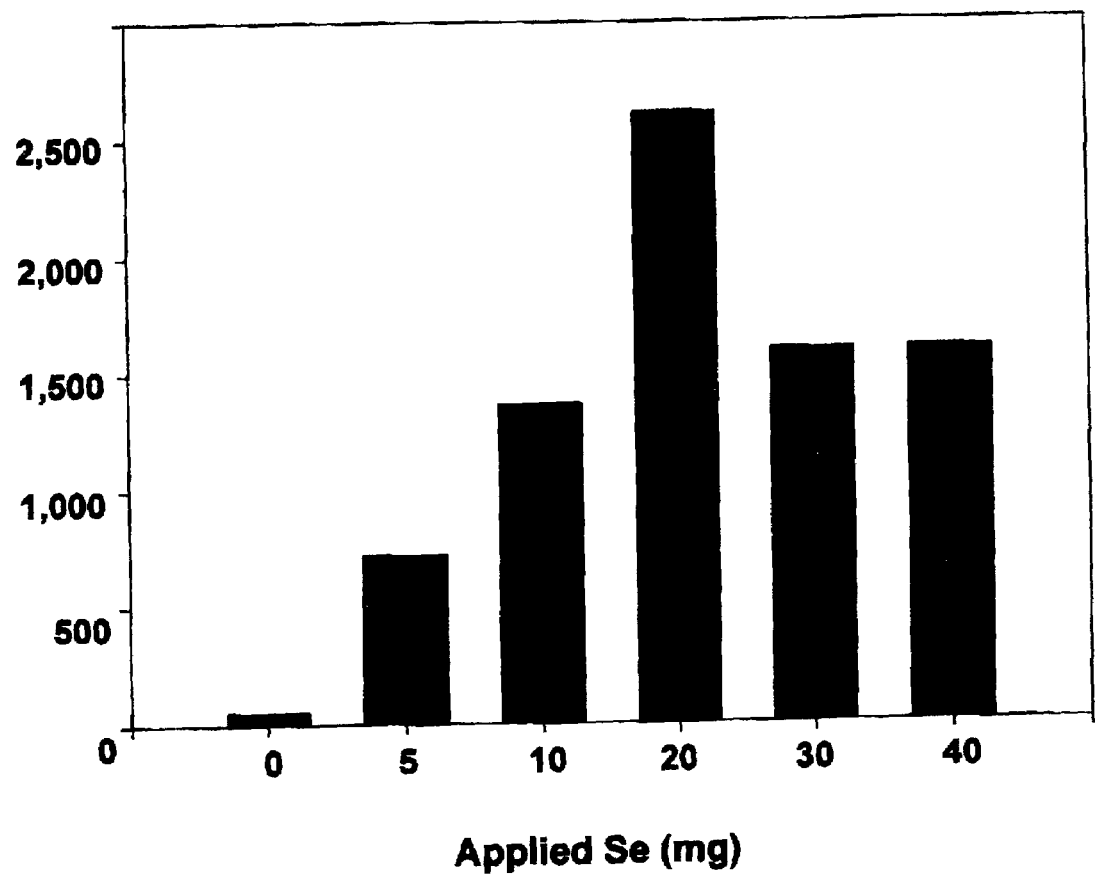
FIG. 4 depicts accumulation of selenium in *Brassica juncea* after growth in a hydroponic system.

Alternatively, the selenocysteine methyl transferase gene from the accumulator species will be cloned by screening the *A. bisulcatus* cDNA library at medium to low stringency with the *A. thaliana* EST clone (22600) (Sambrook et al., In Molecular *Cloning A Laboratory Manual* $2^{nd}$ Edition (ed Irwin N, Nolan C, et al.,), Cold Spring Harbor Laboratory Press, New York, 1989). This *A. thaliana* EST shows 83-84% nucleotide identity to the methionine synthase from a wide variety of unrelated plant species including *Catharanthus roseus* (Madagascar periwinkle), *Mesembryanthemum carystallinum* (common ice plant) and *Solenostemon scutellarioides* (painted nettle), suggesting that the methionine synthase gene is well conserved. This suggests that the *A. thaliana* EST will make a useful probe for cloning the selenocysteine methyl transferase from *Astragalus.*

The A-YES cDNA library from *A. hisulcatus* will be used to screen for clones that allow *E. coli* to grow in the presence of the toxic analogue of cystine, selenocystine (Jacobson and Harrell, 1981). By complementing in an *E. coli* strain containing the F-plasmid expressing the lacl repressor protein, which represses the LacZ promoter, and testing the selenocystine-resistance phenotype for IPTG dependence, we will be able to ensure that the ability to resist selenocystine is encoded by a plant cDNA carried in the A-YES vector. This screen is based on two assumptions: (a) that the cellular toxicity of selenocystine is based on its intracellular conversion to selenocysteine (a conversion catalyzed by NADH cystine reductase); and (b) that selenocysteine can be detoxified by methylation, forming the nonprotein amino acid methylselenocysteine, a conversion performed by selenocysteine methyltransferase.

The *A. bisulcatus* selenocysteine methyl transferase will be expressed in *E. coli* and the identity of the cloned gene as a selenocysteine methyl transferase will be determined by measuring the catalytic properties of the expressed protein. The regulation of expression of the selenocysteine methyl transferase will also be investigated. Antibodies will be raised against the recombinant protein and Northern and Western analysis performed. (Sambrook et al., In *Molecular Cloning A Laboratory Manual* $2^{nd}$ Edition (ed Irwin N, Nolan C, et al.,), Cold Spring Harbor Laboratory Press, New York, 1989).

Cystathionine y synthase has previously been cloned from *A. thaliana* by the functional complementation of an *E. Coli* mutant lacking this gene (MetB; available from the *E. coli* Genetic Stock Center, strain 6172). We propose to use the same technique to clone the cystationine-y-synthase from the accumulator *A. bisulcatus*. We will express our library in the *E. coli* MetB and screen for cDNA's which complement the methionine requirement.

Alternatively the cystathionine y synthase gene from the accumulator species of *Astragalus* will be cloned by screening the *Astragalus* cDNA libraries at medium to low stringency with the *A. thaliana* EST clone (AA713066) (Sambrook et al., In *Molecular Cloning A Laboratory Manual* $2^{nd}$ Edition (ed Irwin N, Nolan C, et al.,), Cold Spring Harbor Laboratory Press, New York, 1989). This *A. thaliana* EST shows 73 and 74% nucleotide identity to the cystathionine y synthase from *Fragaria vesca* (wild strawberry) and *Zea mays* (maize) respectively, showing that this gene is conserved across very divergent plant families. This suggests that the EST will make a useful probe for cloning the cystathionine y synthase from

*B. juncea* will be transformed with the cloned *A. bisulcatus* selenocysteine methyl transferase gene. Expression of the transgene will be determined using Northern and Western blot analysis (Sambrook et al., In *Molecular Cloning A Laboratory Manual* $2^{nd}$ Edition (ed Irwin N, Nolan C, et al.,), Cold Spring Harbor Laboratory Press, New York, 1989). Transgenic plants expressing the transgene will be tested for their ability to synthesis methylselenocystein using x-ray absorption spectroscopy and HPLC analysis. These plants will also be tested for tolerance to selenate (Kramer, Plant *Physiol.* 115:1641, 1997). In addition, tissue extracts of transgenic plants will be assayed for selenocysteine methyl transferase activity. Plants exhibiting varying levels of transgene expression will be chosen for further analysis to determine if a correlation exists between levels of expression and selenate resistance in transgenic *B. juncea*

The molecular speciation of Se in wild-type and transgenic plant expressing the selenocysteine methyl transferase will be compared. We propose to determine the molecular speciation of Se using the non-invasive technique of X-ray absorption spectroscopy (XAS). This approach has been used to successfully speciate Se in sediments (Pickering et al., *Environ. Sci Technol.* 29:2456, 1995). We have also used this approach to identify the various Se species in plants tissues. To confirm the Se speciation obtained using XAS a limited number of plant samples will also be analyzed using reverse phase HPLC following established procedures (Bird et al., *J. Chromatography A,* 789:349, 1997). Plant samples will be extracted in both 10% methanol in 0.2 M HCl and 10 mM phosphate buffer, pH 7.0. Phosphate buffer extracts will be treated will protease XIV, a non-specific protease to release Se-amino acids from proteins. Both extracts will then be derivatized with 2,4-dlinitrofluorbenzene to produce dinitrophenyl (DNP) (Goeger and Ganther, Arch. Biochem. Biophys. 302:222, 1993). DNP-derivatized samples will be applied to reverse phase C18 column, and eluted with a methanol; water (62.38) mobile phase containing 0.024% trifluoracetic acid. By labeling plants with Se we will be able to detect Se containing compounds eluting from the column using an inline radiochemical detector. Se containing compounds will then be identified by their co-elution with standards.

Example 6—Accumulation of Bioavailable Selenium into Hydroponically-grown *Brassica juncea*

*Brassica juncea* plants were grown hydroponically for 4 weeks, at which time five different levels (5, 10, 20, 30, and 40 mg) of sodium selenate were added to the growth medium. Plants were grown for an additional week, at which time shoots were harvested and total Se concentration was determined. As shown in FIG. 4, a maximum concentration of 2,500 mg/kg (0.25% on a dry weight basis) was achieved at the 20 mg treatment level. Further increases in Se treatment did not increase the concentration of Se accumulated into plant shoots.

Figure 5:
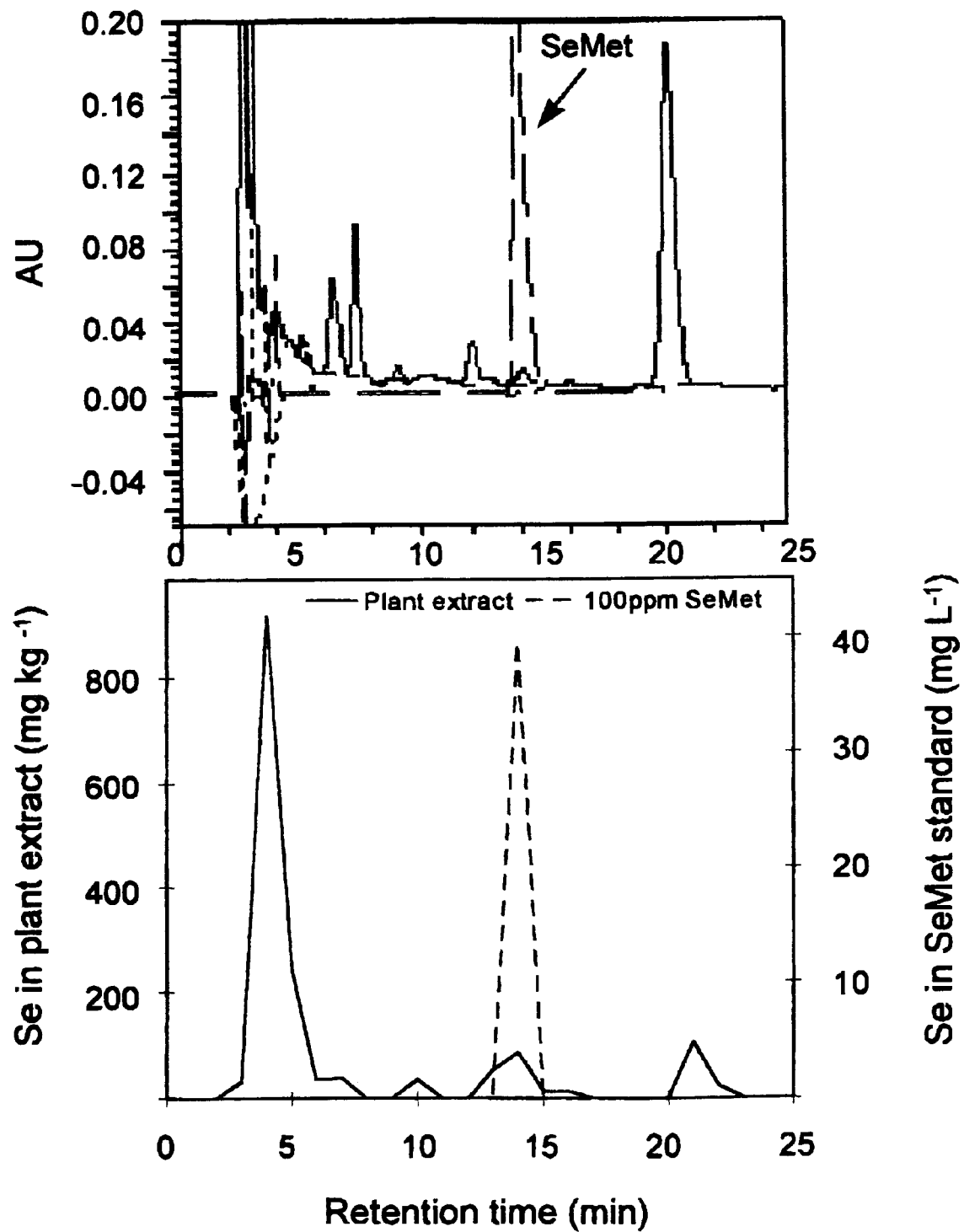
FIG. 5 shows speciation of selenium from plant extracts.
Figure 7:
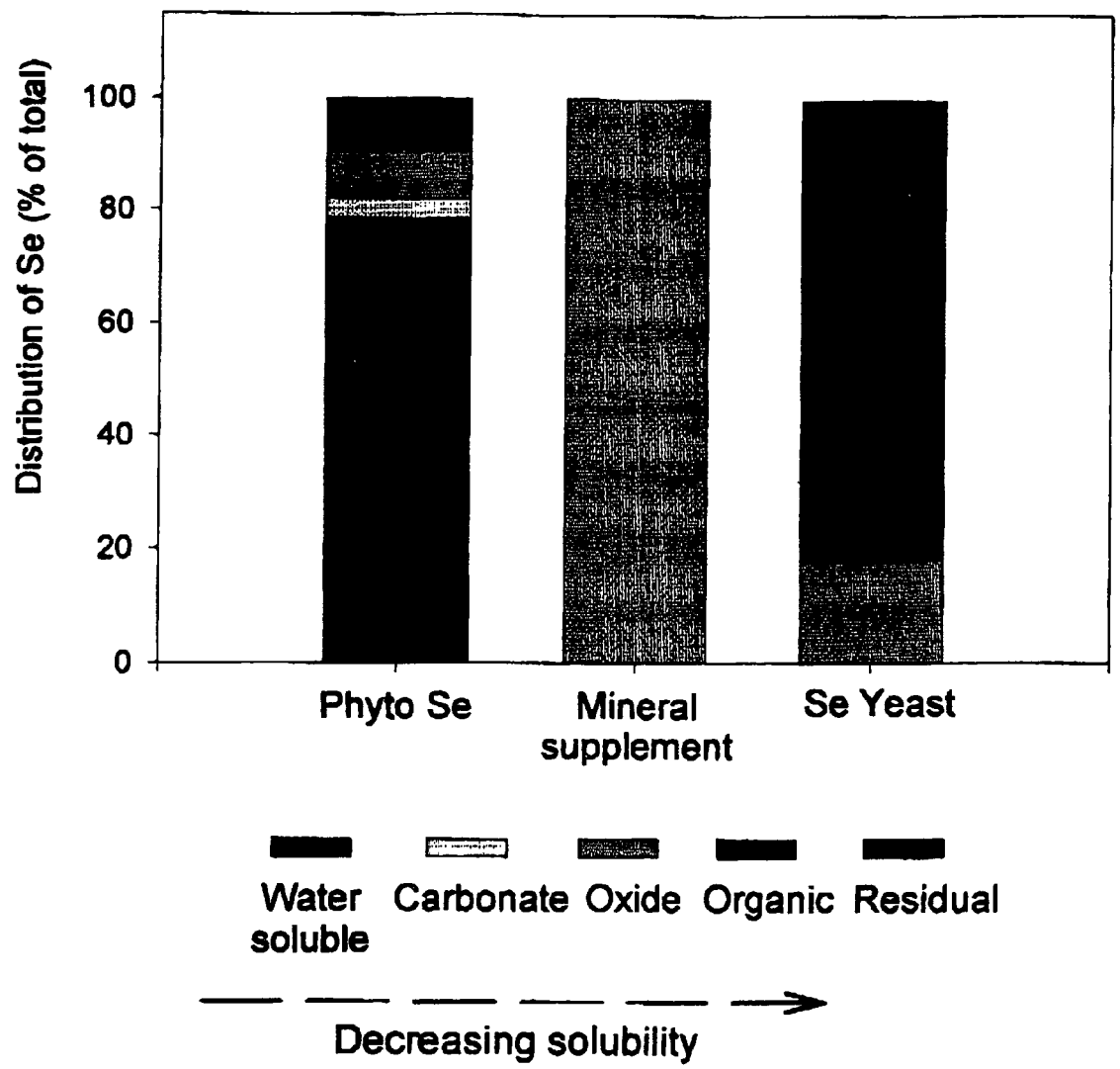

The species of selenium accumulated into the plants was determined through HPLC analysis (see FIG. 5). Specifically, plant extracts were assayed on a C8 HPLC column suing selenoamino acid standards. The chromatography conditions were: mobile phase, 98 water: 2 methanol+0.1% TFA; 220 nm flow rate, 1 ml/min. Fractions were collected during the HPLC run at 1 minute intervals and were analyzed on graphite furnace (GF-AAS) for Se content. SeMet eluted at 14 minutes. Approximately 20% of the Se accumulated in the plant was SeMet.

The solubility of selenium accumulated in these plants was also determined, and was compared with that of selenium in yeast and selenium in a mineral supplement. As shown in FIG. 6, plant Se was the most soluble and yeast Se was the least soluble. Approximately 85% of the Se present in the *B. juncea* shoots were soluble. These findings indicate that Se accumulated in plants is expected to be more bioavailable than other forms of Se. Thus, plants that have accumulated selenium according to the present invention show significant value for use in dietary supplements, as well as for feed for animals.

OTHER EMBODIMENTS

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A nutritional supplement comprising the edible portions of a plant which has been induced to hyperaccumulate selenium in its edible portions, and which has been incorporated into one or more of processed food, a capsule, a tablet, a powder, a gel, and a liquid, wherein the plant is a member of the family Brassicaceae, and wherein the plant hyperaccumulates at least 400 parts per million dry weight of nutritionally valuable selenium in at least some of its edible portions.

2. The nutritional supplement of claim 1, wherein the inducing agent is an organic acid.

3. The nutritional supplement of claim 2, wherein the inducing agent is selected from a group consisting of citric acid, acetic acid, malic acid, salicylic acid and succinic acid.

4. A nutritional supplement according to claim 1, wherein the accumulated selenium is in the form of Se-methylselenocysteine.

5. The nutritional supplement of claim 4, wherein the inducing agent is an organic acid.

6. The nutritional supplement of claim 4, wherein the inducing agent is selected from a group consisting of citric acid, acetic acid, malic acid, salicylic acid and succinic acid.

* * * * *